United States Patent [19]
Ota et al.

[11] Patent Number: 6,162,832
[45] Date of Patent: Dec. 19, 2000

[54] 2-PHENOXYANILINE DERIVATIVES

[75] Inventors: Tomomi Ota; Misa Nakanishi; Izumi Aibe; Minoru Taguchi; Kazuyuki Tomisawa, all of Tokyo, Japan

[73] Assignee: Taisho Pharmaceutical Co., Inc., Tokyo, Japan

[21] Appl. No.: 09/529,218

[22] PCT Filed: Oct. 20, 1998

[86] PCT No.: PCT/JP98/04729

§ 371 Date: Apr. 10, 2000

§ 102(e) Date: Apr. 10, 2000

[87] PCT Pub. No.: WO99/20598

PCT Pub. Date: Apr. 29, 1999

[30] Foreign Application Priority Data

Oct. 20, 1997 [JP] Japan ................................. 9-286623

[51] Int. Cl.$^7$ .................................................. A61K 31/135
[52] U.S. Cl. ........................................... 514/646; 564/430
[58] Field of Search ............................. 564/430; 514/646

[56] References Cited

U.S. PATENT DOCUMENTS 5,556,860  9/1996  Muraoka et al. .

FOREIGN PATENT DOCUMENTS

| | | |
|---|---|---|
| 5-194400 | 8/1993 | Japan . |
| 7-41465 | 2/1995 | Japan . |
| 9-09306 | 3/1997 | Japan . |
| 10-218844 | 8/1998 | Japan . |

*Primary Examiner*—Samuel Barts
*Attorney, Agent, or Firm*—Pillsbury, Madison & Sutro, LLP

[57] ABSTRACT

A 2-phenoxyaniline derivative represented by the formula:

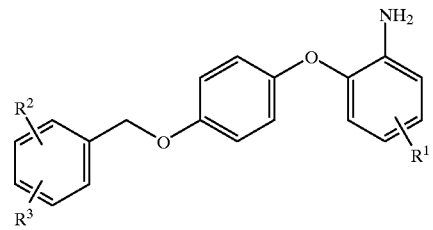

wherein $R^1$ is a hydrogen atom or a lower alkoxy group, $R^2$ is a halogen atom or a nitro group, and $R^3$ is a hydrogen atom or a halogen atom, or a pharmaceutically acceptable salt thereof.

12 Claims, No Drawings

2-PHENOXYANILINE DERIVATIVES

This application is a 371 of PCT/JP98/04729 filed Oct. 20, 1998.

TECHNICAL FIELD

The present invention relates to 2-phenoxyaniline derivatives having an inhibitory action on a $Na^+/Ca^{2+}$ exchange system.

BACKGROUND ART

Among prior art compounds which inhibit a $Na^+/Ca^{2+}$ exchange system selectively and prevent overload of $Ca^{2+}$ in cells regarded as important in the cell injury mechanism after ischemia or reperfusion, there are known compounds as described in Japanese Patent Kokai 7-41465 and WO97/09306. However, there have not been known any compounds with a phenoxyaniline skeleton which have an inhibitory action on a $Na^+/Ca^{2+}$ exchange system.

DISCLOSURE OF THE INVENTION

As a result of extensive researches on the compounds having an inhibitory action on a $Na^+/Ca^{2+}$ exchange system, the present inventors have found that some kind of compounds having a phenoxyaniline skeleton meet said object, and the present invention has been accomplished based on the finding.

That is, the present invention is directed to a 2-phenoxyaniline derivative represented by Formula (1):

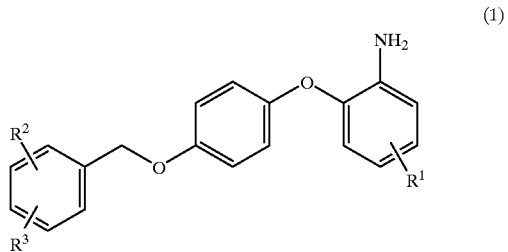

(1)

wherein $R^1$ is a hydrogen atom or a lower alkoxy group, $R^2$ is a halogen atom or a nitro group, and $R^3$ is a hydrogen atom or a halogen atom, or a pharmaceutically acceptable salt thereof.

Furthermore, the present invention is directed to a pharmaceutical composition containing the above-mentioned compound or the pharmaceutically acceptable salt thereof as an effective component.

Furthermore, the present invention is directed to a pharmaceutical composition for the treatment or prevention of ischemic heart diseases, ischemic cerebral diseases or ischemic renal diseases containing the above-mentioned compound or the pharmaceutically acceptable salt thereof as an effective component.

Furthermore, the present invention is directed to use of the above-mentioned compound or the pharmaceutically acceptable salt thereof for the manufacture of a pharmaceutical composition for the treatment or prevention of ischemic heart diseases, ischemic cerebral diseases or ischemic renal diseases.

Furthermore, the present invention is directed to a method for the treatment or prevention of ischemic heart diseases, ischemic cerebral diseases or ischemic renal diseases which includes the step of administering a pharmacologically effective amount of the above-mentioned compound or the pharmaceutically acceptable salt thereof to a human.

Furthermore, the present invention is directed to a pharmaceutical composition for the protection of cells during thrombolytic therapy, angioplasty, bypass operation of coronary artery or organ transplantation containing the above-mentioned compound or the pharmaceutically acceptable salt thereof as an effective component.

Furthermore, the present invention is directed to use of the above-mentioned compound or the pharmaceutically acceptable salt thereof for the manufacture of a pharmaceutical composition for the protection of cells during thrombolytic therapy, angioplasty, bypass operation of coronary artery or organ transplantation.

Furthermore, the present invention is directed to a method for the protection of cells during thrombolytic therapy, angioplasty, bypass operation of coronary artery or organ transplantation which includes the step of administering a pharmacologically effective amount of the above-mentioned compound or the pharmaceutically acceptable salt thereof to a human.

In the present invention, the lower alkoxy group refers to a straight or branched $C_{1-6}$ alkoxy group, and specific examples thereof are a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a 1-methylbutoxy group, a 2-methylbutoxy group, a 1,2-dimethylpropoxy group, a hexyloxy group and an isohexyloxy group.

The halogen atom refers to a fluorine atom, a chlorine atom, a bromine atom or an iodine atom.

In the present invention, preferred phenoxyaniline derivatives are compounds of Formula (1) wherein $R^1$ is an ethoxy group or a propoxy group, in view of the inhibitory action on a $Na^+/Ca^{2+}$ exchange system.

$R^2$ and $R^3$ are preferably the same or different, and are each a halogen atom, and more preferably a fluorine atom.

The compounds of the present invention can be prepared, for example, according to the following preparation scheme (wherein $R^1$, $R^2$ and $R^3$ are as defined above, X is a fluorine atom or a chlorine atom, and Y is a chlorine atom, a bromine atom or an iodine atom).

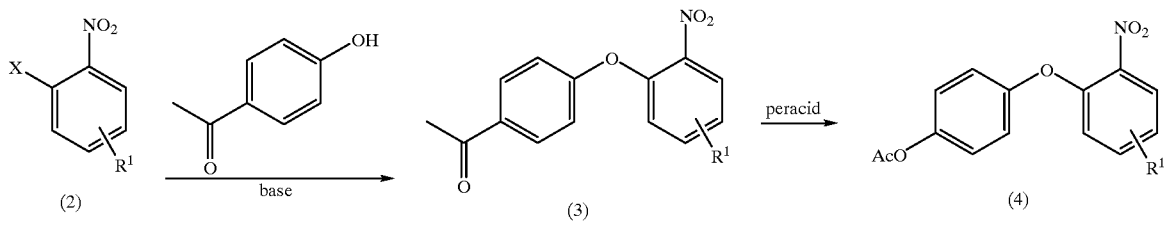

-continued

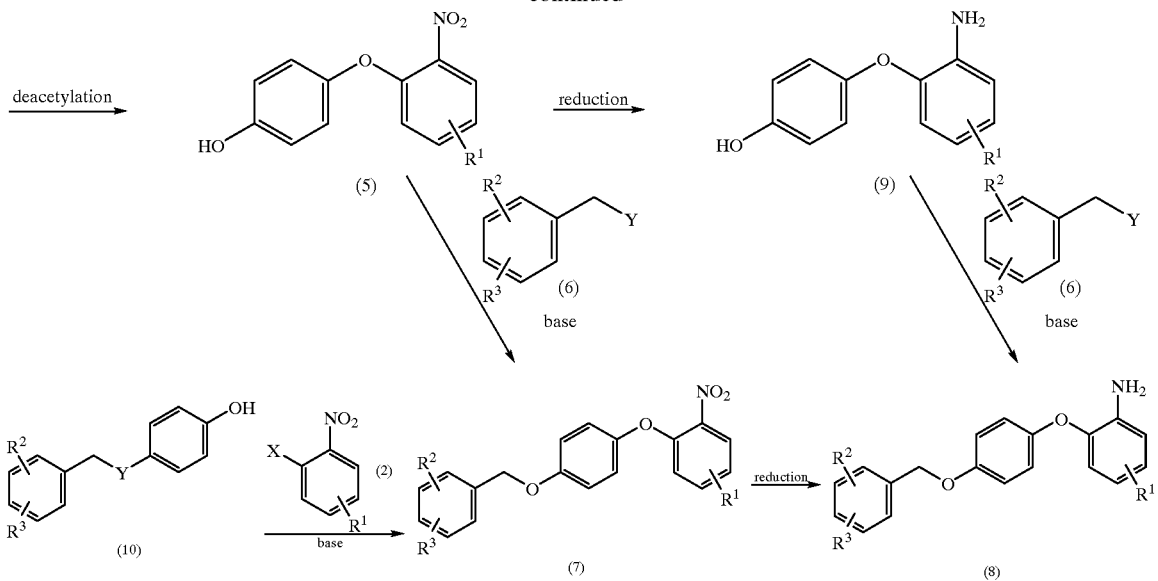

That is, a compound represented by Formula (2) and 4-hydroxyacetophenone are reacted in the presence of a base to give a compound represented by Formula (3).

Examples of the base to be used herein are organic and inorganic bases such as potassium tert-butoxide, sodium hydroxide and sodium hydride. As a reaction solvent can be used N,N-dimethylformamide, tetrahydrofuran, etc. The reaction temperature is from room temperature to the reflux temperature.

Then, the compound represented by Formula (3) is reacted with a peracid to give a compound represented by Formula (4).

Examples of the peracid to be used herein are m-chloroperbenzoic acid and peracetic acid. As a reaction solvent can be used herein chloroform, methylene chloride, etc. The reaction temperature is from 0° C. to room temperature.

The compound represented by Formula (4) is deacetylated in the presence of a base to give a compound represented by Formula (5).

Examples of the base to be used herein are sodium hydroxide, potassium hydroxide and potassium carbonate. As a reaction solvent can be used water, methanol, ethanol, etc., and they can be used alone or in admixture. The reaction temperature is preferably from 0° C. to the reflux temperature.

The compound represented by Formula (5) is reacted with a compound represented by Formula (6) in the presence of a base to give a compound represented by Formula (7).

Examples of the base to be used herein are organic and inorganic bases such as potassium tert-butoxide, sodium hydroxide, sodium hydride and potassium carbonate. As a reaction solvent can be used acetone, N,N-dimethylformamide, tetrahydrofuran, etc. The reaction temperature is from room temperature to the reflux temperature.

The compound represented by Formula (7) is reduced to give a compound (8) of the present invention.

As a reducing agent can be used herein iron-ammonium chloride, iron-acetic acid, palladium carbon-hydrogen, lithium aluminum hydride, nickel chloride-sodium borohydride, etc. As a reaction solvent can be used herein water, methanol, ethanol, tetrahydrofuran, etc., and they can be used alone or in admixture. The reaction temperature is preferably from 0° C. to the reflux temperature.

Furthermore, if necessary, the compound represented by Formula (5) is reduced to give a compound represented by Formula (9), which is then reacted with the compound represented by Formula (6) in the presence of a base, thereby the compound of the present invention represented by Formula (8) can be obtained.

Examples of the base to be used herein are organic and inorganic bases such as potassium tert-butoxide, sodium hydroxide, sodium hydride and potassium carbonate. As a reaction solvent can be used herein acetone, N,N-dimethylformamide, tetrahydrofuran, etc. The reaction temperature is from room temperature to the reflux temperature.

If necessary, the compound (8) of the present invention can be also obtained by protecting the amino group of the compound represented by Formula (9) with an ordinary protective group such as a tert-butoxycarbonyl group and an acetyl group, and reacting the resulting compound with the compound represented by Formula (6), followed by deprotection.

Furthermore, the compound represented by Formula (7) can be also obtained by reacting a compound represented by Formula (10) with the compound represented by Formula (2) in the presence of a base.

Examples of the base to be used herein are organic and inorganic bases such as potassium tert-butoxide, sodium hydroxide and sodium hydride. As a reaction solvent can be used herein N,N-dimethylformamide, tetrahydrofuran, etc. The reaction temperature is from room temperature to the reflux temperature.

The compound represented by Formula (9) can be also prepared according to the following preparation scheme.

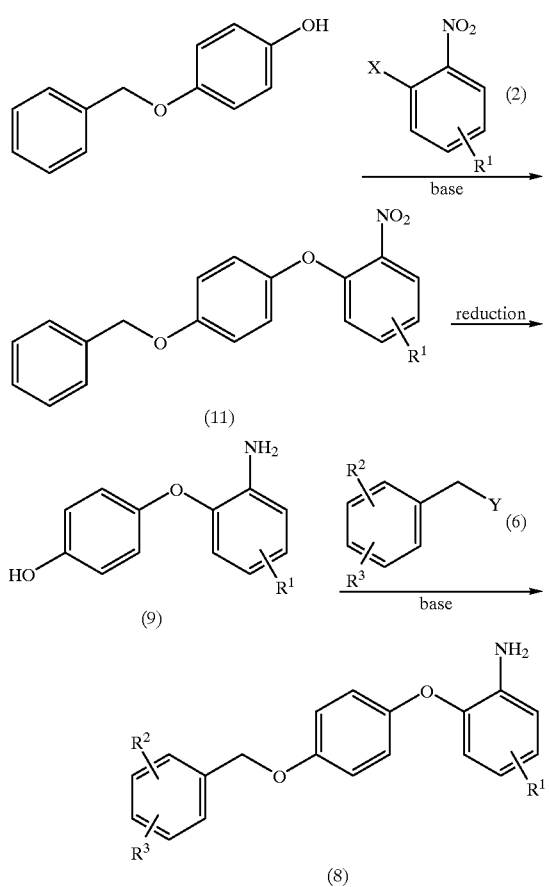

(wherein $R^1$, $R^2$, $R^3$, X and Y are as defined above).

That is, the compound represented by Formula (2) is reacted with 4-(benzyloxy)phenol in the presence of a base to give a compound represented by Formula (11).

Examples of the base to be used herein are organic and inorganic bases such as potassium tert-butoxide, sodium hydroxide and sodium hydride. As a reaction solvent can be used herein N,N-dimethylformamide, tetrahydrofuran, etc. The reaction temperature is from room temperature to the reflux temperature.

Then, the compound represented by Formula (11) is reduced to give the compound represented by Formula (9).

As a reducing agent can be used herein a metal catalyst such as palladium-carbon, platinum oxide, etc. under a hydrogen gas atmosphere. As a solvent can be used herein methanol, ethanol, acetic acid, etc., and if necessary, they are used as a mixture with N,N-dimethylformamide, tetrahydrofuran, etc. The reaction temperature is from 0° C. to the reflux temperature.

The compound of the present invention can be administered orally or parenterally in appropriate dosage forms (tablets, pills, capsules, granules, dry-syrups, injectable preparations, etc.) which are prepared using appropriate known carriers and diluents.

The solid preparations can be produced by using various additives (e.g., a filler, a disintegrator, a binder, a lubricant, a coating agent, etc.) according to agitation granulation, fluidized bed granulation or disintegration granulation.

If necessary, an anti-oxidant, a coating agent, a coloring agent, a corrigent, a surface active agent, a plasticizer and others can be added.

The dose of the effective component of the pharmaceutical preparation according to the present invention can be varied depending on the age, body weight or administration route, but it is usually from 0.1 to 1000 mg/day to an adult, which can be administered in a single dose or divided doses.

INDUSTRIAL APPLICABILITY

The compounds of the present invention inhibit a $Na^+$/$Ca^{2+}$ exchange system effectively, thus, they inhibit overload of $Ca^{2+}$ in cells, prevent the cell injury after ischemia or reperfusion, are useful for the treatment or prevention of ischemic heart diseases (e.g. myocardial infarction), ischemic cerebral diseases (e.g. cerebral infarction) or ischemic renal diseases, and further effective on the protection of cells during surgical treatments such as thrombolytic therapy, angioplasty, bypass operation of coronary artery and organ transplantation.

BEST MODE OF CARRYING OUT THE INVENTION

The present invention is illustrated in more detail by the following reference examples, examples and experiment. Furthermore, the structural formula of the compounds prepared in Examples 1 to 17 is shown in Table 1.

TABLE 1

Structural Formula

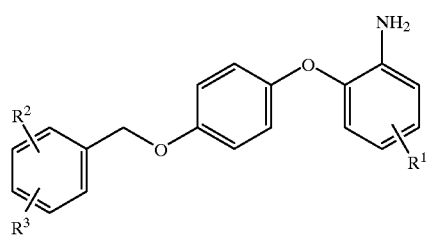

| Compound No. | $R^1$ | $R^2$ | $R^3$ | |
|---|---|---|---|---|
| 1 | H | 3-F | 4-F | hydrochloride |
| 2 | H | 3-F | 5-F | hydrochloride |
| 3 | H | 2-F | 3-F | hydrochloride |
| 4 | H | 2-F | 5-F | hydrochloride |
| 5 | H | 2-F | 6-F | hydrochloride |
| 6 | 5-$OCH_2CH_3$ | 2-F | 5-F | hydrochloride |
| 7 | 5-$OCH_2CH_3$ | 2-F | 6-F | hydrochloride |
| 8 | H | 2-F | 4-F | hydrochloride |
| 9 | 5-$OCH_2CH_3$ | 3-F | H | — |
| 10 | 5-$OCH_2CH_3$ | 2-F | 3-F | hydrochloride |
| 11 | 5-$OCH_2CH_3$ | 2-F | 4-F | hydrochloride |
| 12 | 5-$OCH_2CH_3$ | 3-F | 4-F | hydrochloride |
| 13 | 5-$OCH_2CH_3$ | 3-F | 5-F | hydrochloride |
| 14 | 5-$OCH(CH_3)_2$ | 2-F | 5-F | hydrochloride |
| 15 | H | 3-$NO_2$ | H | hydrochloride |
| 16 | H | 2-F | H | hydrochloride |
| 17 | H | 2-Cl | 5-Cl | hydrochloride |

REFERENCE EXAMPLE 1

4-(3,4-Difluorobenzyloxy)phenol (1) To a solution of 3,4-difluorobenzyl bromide (7.94 g, 38 mmol) and 4-hydroxyacetophenone (5.22 g, 38 mmol) in N,N-dimethylformamide (50 ml) was added potassium carbonate (6.00 g, 43 mmol), followed by stirring for 20 hours. The reaction solution was poured into water and extracted with ethyl acetate, and the organic layer was washed with water and a saturated aqueous sodium chloride solution and dried. The solvent was evaporated under reduced pressure, and the residue was purified by silica gel column chromatography [eluent; hexane-ethyl acetate (4:1)] to give 4-(3,4-difluorobenzyloxy)acetophenone (9.75 g).

$^1$H-NMR (CDCl$_3$, 200 MHz) δ (ppm); 2.54 (s, 3H), 5.07 (s, 2H), 6.98 (d, J=9 Hz, 2H), 7.10–7.33 (m, 3H), 7.94 (d, J=9 Hz, 2H).

(2) To a solution of 4-(3,4-difluorobenzyloxy) acetophenone (9.03 g, 34.5 mmol) in chloroform (50 ml) was added m-chloroperbenzoic acid (5.95 g, 34.5 mmol), followed by stirring at room temperature for 20 hours. To the reaction solution was added m-chloroperbenzoic acid (1.07 g, 6.2 mmol), followed by stirring at room temperature for 3 days. The precipitated insoluble matter was removed by filtration, and the filtrate was washed with an aqueous sodium thiosulfate solution, an aqueous sodium bicarbonate solution, water and a saturated aqueous sodium chloride solution, successively, and dried. The solvent was evaporated under reduced pressure, and the resulting crude crystals were recrystallized from ethanol to give 4-(3,4-difluorobenzyloxy)phenyl acetate (6.97 g).

$^1$H-NMR (CDCl$_3$, 200 MHz) δ (ppm); 2.28 (s, 3H), 5.00 (s, 2H), 6.93 (d, J=9 Hz, 2H), 7.02 (d, J=9 Hz, 2H), 7.08–7.30 (m, 3H).

(3) To a solution of 4-(3,4-difluorobenzyloxy)phenyl acetate (6.77 g, 24.4 mmol) in methanol (100 ml) was added potassium carbonate (3.36 g, 24.3 mmol), followed by reflux for 3 hours. After allowing to stand overnight, the reaction solution was poured into water, made acidic with hydrochloric acid and extracted with chloroform. The solvent was evaporated under reduced pressure to give the title compound (5.68 g), which was used for the following reaction without purification.

$^1$H-NMR (CDCl$_3$, 200 MHz) δ (ppm); 4.54 (s, 1H), 4.94 (s, 2H), 6.75 (d, J=9 Hz, 2H), 6.84 (d, J=9 Hz, 2H), 7.06–7.29 (m, 3H).

The following compounds of Reference Examples 2 to 6 were synthesized in the same manner as in Reference Example 1.

REFERENCE EXAMPLE 2

4-(3,5-Difluorobenzyloxy)phenol $^1$H-NMR (CDCl$_3$, 200 MHz) δ (ppm); 4.45 (s, 1H), 4.99 (s, 2H), 6.68–6.88 (m, 5H), 6.95 (dd, J=2, 9 Hz, 2H).

REFERENCE EXAMPLE 3

4-(2,3-Difluorobenzyloxy)phenol $^1$H-NMR (CDCl$_3$, 200 MHz) δ (ppm); 4.45 (bs, 1H), 5.09 (s, 2H), 6.76 (d, J=9 Hz, 2H), 6.87 (d, J=9 Hz, 2H), 7.03–7.33 (m, 3H).

REFERENCE EXAMPLE 4

4-(2,5-Difluorobenzyloxy)phenol $^1$H-NMR (CDCl$_3$, 200 MHz) δ (ppm); 4.58 (bs, 1H), 5.05 (s, 2H), 6.76 (d, J=9 Hz, 2H), 6.87 (d, J=9 Hz, 2H), 6.93–7.10 (m, 2H), 7.18–7.28 (m, 1H).

REFERENCE EXAMPLE 5

4-(2,6-Difluorobenzyloxy)phenol $^1$H-NMR (CDCl$_3$, 200 MHz) δ (ppm); 4.62 (bs, 1H), 5.06 (s, 2H), 6.76 (d, J=9 Hz, 2H), 6.85–7.00 (m, 4H), 7.25–7.40 (m, 1H).

REFERENCE EXAMPLE 6

4-(2,4-Difluorobenzyloxy phenol $^1$H-NMR (CDCl$_3$, 200 MHz) δ (ppm); 4.51 (s, 1H), 5.01 (s, 2H), 6.72–6.95 (m, 6H), 7.46 (dt, J=6, 9 Hz, 1H).

REFERENCE EXAMPLE 7

4-(2-Nitrophenoxy)phenol (1) To a solution of 4-hydroxyacetophenone (5.44 g, 40 mmol) in N,N-dimethylformamide (70 ml) was added potassium tert-butoxide (4.48 g, 40 ml), followed by stirring for 30 minutes. Then, 1-fluoro-2-nitrobenzene (5.64 g, 40 mmol) was added, followed by stirring at 150° C. for 8 hours. After allowing to stand overnight, the reaction solution was further stirred at 150° C. for 6 hours, poured into water and extracted with ethyl acetate. The organic layer was washed with water and a saturated aqueous sodium chloride solution and dried. The solvent was evaporated under reduced pressure, and the residue was purified by silica gel column chromatography (eluent; chloroform) to give 4-(2-nitrophenoxy)acetophenone (7.41 g)

$^1$H-NMR (CDCl$_3$, 200 MHz) δ (ppm); 2.59 (s, 3H), 7.04 (d, J=9 Hz, 2H), 7.18 (d, J=8 Hz, 1H), 7.35 (t, J=8 Hz, 1H), 7.63 (t, J=8 Hz, 1H), 7.99 (d, J=9 Hz, 2H), 8.04 (d, J=8 Hz, 1H).

(2) To a solution of 4-(2-nitrophenoxy)acetophenone (7.14 g, 27.8 mmol) in methylene chloride (100 ml) was added m-chloroperbenzoic acid (5.27 g, 30.6 mmol), followed by stirring at room temperature for 48 hours. The reaction solution was diluted with chloroform, washed with an aqueous sodium thiosulfate solution, an aqueous sodium carbonate solution, water and a saturated aqueous sodium chloride solution, successively, and dried. The solvent was evaporated under reduced pressure, and the residue was purified by silica gel column chromatography [eluent; ethyl acetate-hexane (1:9)] to give 4-(2-nitrophenoxy)phenyl acetate (6.37 g).

$^1$H-NMR (CDCl$_3$, 200 MHz) δ (ppm); 2.31 (s, 3H), 7.03–7.25 (m, 6H), 7.53 (t, J=8 Hz, 1H), 7.96 (d, J=8 Hz, 1H)

(3) To a solution of 4-(2-nitrophenoxy)phenyl acetate (6.32 g, 23.2 mmol) in methanol (100 ml) was added potassium carbonate (6.39 g, 46.3 mmol), followed by reflux for 3 hours. The reaction solution was poured into water, made acidic with hydrochloric acid and extracted with chloroform. The organic layer was washed with water and a saturated aqueous sodium chloride solution and dried. The solvent was evaporated under reduced pressure to give the title compound (5.35 g).

$^1$H-NMR (CDCl$_3$, 200 MHz) δ (ppm); 4.98 (bs, 1H), 6.85 (d, J=9 Hz, 2H), 6.89 (d, J=8 Hz, 1H), 6.97 (d, J=9 Hz, 2H), 7.14 (t, J=8 Hz, 1H), 7.47 (t, J=8 Hz, 1H), 7.93 (d, J=8 Hz, 1H)

REFERENCE EXAMPLE 8

1-Chloro-4-ethoxy-2-nitrobenzene

To a solution of 4-chloro-3-nitrophenol (5.21 g, 30 mmol) in acetone (60 ml) were added ethyl iodide (5.94 g, 38 mmol) and potassium carbonate (4.53 g, 33 mmol), followed by stirring at 50° C. for 5 hours. After allowing to stand overnight, the reaction solution was poured into water and extracted with ethyl acetate. The organic layer was washed with water and a saturated aqueous sodium chloride solution and dried, and the solvent was evaporated under reduced pressure. The residue was purified by silica gel column chromatography [eluent; ethyl acetate-hexane (1:4)] to give the title compound (5.72 g).

m.p. 48–49.5° C.

REFERENCE EXAMPLE 9

1-Chloro-4-isopropoxy-2-nitrobenzene

The title compound was obtained from 4-chloro-3-nitrophenol and 2-iodopropane in the same manner as in Reference Example 8.

$^1$H-NMR (CDCl$_3$, 200 MHz) δ (ppm); 1.35 (d, J=6 Hz, 6H), 4.56 (sext, J=6 Hz, 1H), 7.03 (dd, J=3, 9 Hz, 1H), 7.36 (d, J=3 Hz, 1H), 7.41 (d, J=9 Hz, 1H)

REFERENCE EXAMPLE 10

5-Ethoxy-2-(4-hydroxyphenoxy)aniline (1) To a solution of 4-(benzyloxy)phenol (5.68 g, 28.4 mmol) in N,N-dimethylformamide (100 ml) was added potassium tert-butoxide (3.50 g, 31.2 mmol), and after stirring for 10 minutes, 1-chloro-4-ethoxy-2-nitrobenzene (5.73 g, 28.4 mmol) was added to the reaction solution, followed by stirring at 150° C. for 2 hours. The reaction solution was cooled to room temperature, poured into water and extracted with ethyl acetate. The organic layer was washed with water and a saturated aqueous sodium chloride solution, and after drying, the solvent was evaporated under reduced pressure. The resulting crude crystals were recrystallized from methanol to give 4-[4-(benzyloxy)phenoxy]-3-nitrophenetole (7.18 g).

m.p. 96–96.5° C.

(2) To a solution of 4-[4-(benzyloxy)phenoxy]-3-nitrophenetole (4.26 g, 11.7 mmol) in a mixture of ethanol (70 ml) and tetrahydrofuran (50 ml) was added 10% palladium-carbon (430 mg), followed by stirring under a hydrogen gas atmosphere at room temperature overnight. After removal of the insoluble matter by filtration, the solvent was evaporated under reduced pressure. The resulting crude crystals were recrystallized from a mixture of ethyl acetate and hexane (1:9) to give the title compound (2.63 g).

$^1$H-NMR (DMSO-d$_6$, 200 MHz) δ (ppm); 1.30 (t, J=6 Hz, 3H), 3.90 (q, J=6 Hz, 2H), 4.80 (bs, 2H), 6.05 (dd, J=2, 8 Hz, 1H), 6.35 (d, J=2 Hz, 1H), 6.60 (d, J=8 Hz, 1H), 6.65–6.77 (m, 4H), 9.05 (s, 1H)

REFERENCE EXAMPLE 11

2-4-(Hydroxyphenoxy)-5-methoxyaniline

The title compound was obtained from 4-(benzyloxy)phenol and 4-chloro-3-nitroanisole in the same manner as in Reference Example 10.

m.p. 105–106° C.

REFERENCE EXAMPLE 12

2-4-(Hydroxyphenoxy)aniline

The title compound was obtained from 4-(benzyloxy)phenol and 1-fluoro-2-nitrobenzene in the same manner as in Reference Example 10.

$^1$H-NMR (DMSO-d$_6$, 200 MHz) δ (ppm); 4.84 (s, 2H), 6.48 (dt, J=2, 8 Hz, 1H), 6.63 (dd, J=2, 8 Hz, 1H), 6.67–6.87 (m, 6H), 9.16 (s, 1H)

EXAMPLE 1

2-[4-(3.4-Difluorobenzyloxy)phenoxy]aniline hydrochloride (1) To a solution of 4-(3,4-difluorobenzyloxy)phenol (1.00 g, 4.2 mmol) in N,N-dimethylformamide (20 ml) was added potassium tert-butoxide (0.47 g, 4.2 mmol), followed by stirring at room temperature for 30 minutes. To the reaction solution was added 1-fluoro-2-nitrobenzene (0.60 g, 4.3 mmol), followed by stirring at 150° C. for 5 hours. After allowing to stand overnight, the reaction solution was poured into water and extracted with ethyl acetate. The organic layer was washed with water and a saturated aqueous sodium chloride solution and dried. The solvent was evaporated under reduced pressure, and the residue was purified by silica gel column chromatography (eluent; chloroform) to give 1-[4-(3,4-difluorobenzyloxy)phenoxy]-2-nitrobenzene (1.41 g).

m.p. 74–75° C.

(2) To a solution of 1-[4-(3,4-difluorobenzyloxy) phenoxy]-2-nitrobenzene (0.96 g, 2.7 mmol) in ethanol (50 ml) were an iron powder (0.75 g, 13.4 mg-atom) and a solution of ammonium chloride (0.09 g, 1.7 mmol) in water (10 ml), followed by reflux for 3 hours. The reaction solution was cooled to room temperature, and after removal of the insoluble matter by filtration, the solvent was evaporated under reduced pressure. The residue was dissolved in ethyl acetate and dried over magnesium sulfate. After removal of the drying agent, 4 N hydrogen chloride-ethyl acetate solution (2 ml) was added, followed by stirring for 30 minutes. The precipitated crystals were collected by filtration and dried to give the title compound (0.92 g).

m.p. 195–196° C.

The following compounds of Examples 2 to 14 were synthesized in the same manner as in Example 1.

EXAMPLE 2

2-[4-(3,5-Difluorobenzyloxy)phenoxy]aniline hydrochloride m.p. 174.5–176.5° C.

EXAMPLE 3

2-[4-(2,3-Difluorobenzyloxy)phenoxy]aniline hydrochloride m.p. 178.5–179.5° C.

EXAMPLE 4

2-[4-(2,5-Difluorobenzyloxy)phenoxy]aniline hydrochloride $^1$H-NMR (DMSO-d$_6$, 200 MHz) δ (ppm); 5.13 (s, 2H), 6.78 (dd, J=2, 8 Hz, 1H), 7.03–7.18 (m, 6H), 7.25–7.50 (m, 4H)

EXAMPLE 5

2-[4-(2,6-Difluorobenzyloxy)phenoxy]aniline hydrochloride m.p. 163.6–166.4° C.

EXAMPLE 6

2-[4-(2.5-Difluorobenzyloxy)phenoxy]-5-ethoxyaniline hydrochloride $^1$H-NMR (DMSO-d$_6$, 200 MHz) δ (ppm); 1.31 (t, J=7.0 Hz, 3H), 3.96 (q, J=7.0 Hz, 2H), 5.10 (s, 2H), 6.38–7.50 (m, 10H)

EXAMPLE 7

2-[4-(2.6-Difluorobenzyloxy)phenoxy]-5-ethoxyaniline hydrochloride m.p. 199–200.5° C.

EXAMPLE 8

2-[4-(2,4-Difluorobenzyloxy)phenoxy]aniline hydrochloride m.p. 181.5–183° C.

EXAMPLE 9

5-Ethoxy-2-[4-(3-fluorobenzyloxy)phenoxy]aniline $^1$H-NMR (CDCl$_3$, 200 MHz) δ (ppm); 1.39 (t, J=7.0 Hz, 3H), 3.77 (brs, 2H), 3.98 (q, J=7.0 Hz, 2H), 5.02 (s, 2H), 6.25 (dd, J=2.9, 8.8 Hz, 1H), 6.37 (d, J=2.9 Hz, 1H), 6.77 (d, J=8.8 Hz, 1H), 6.95–7.06 (m, 1H), 7.11–7.22 (m, 2H), 7.35 (dt, J=5.9, 7.9 Hz, 1H)

EXAMPLE 10

2-[4-(2,3-Difluorobenzyloxy)phenoxy]-5-ethoxyaniline hydrochloride $^1$H-NMR (DMSO-d$_6$, 200 MHz) δ (ppm); 1.31 (t, J=7 Hz, 3H), 3.97 (q, J=7 Hz, 2H), 5.17 (s, 2H), 6.65 (dd, J=3, 9 Hz, 1H), 6.79 (d, J=9 Hz, 1H), 6.91 (d, J=3 Hz, 1H), 6.98 (d, J=9 Hz, 2H), 7.07 (d, J=9 Hz, 2H), 7.21–7.53 (m, 3H)

EXAMPLE 11

2-[4-(2.4-Difluorobenzyloxy)phenoxy]-5-ethoxyaniline hydrochloride $^1$H-NMR (DMSO-d$_6$, 200 MHz) δ (ppm); 1.30 (t, J=7 Hz, 3H), 3.96 (q, J=7 Hz, 2H), 5.07 (s, 2H), 6.60 (dd, J=3, 9 Hz, 1H), 6.77 (d, J=9 Hz, 1H), 6.83 (d, J=3 Hz, 1H), 6.95 (d, J=9 Hz, 2H), 7.05 (d, J=9 Hz, 2H), 7.14 (dt, J=3, 7 Hz, 1H), 7.32 (dt, J=3, 9 Hz, 1H), 7.63 (dt, J=7, 9 Hz, 1H)

EXAMPLE 12

2-[4-(3.4-Difluorobenzyloxy)phenoxy]-5-ethoxyaniline hydrochloride $^1$H-NMR (DMSO-d$_6$, 200 MHz) δ (ppm); 1.30 (t, J=6 Hz, 3H), 3.96 (q, J=6 Hz, 2H), 5.04 (s, 1H), 6.47–6.56 (m, 1H), 6.70–6.78 (m, 2H), 6.97 (d, J=7 Hz, 2H), 7.02 (d, J=7 Hz, 2H), 7.26–7.36 (m, 1H), 7.39–7.59 (m, 2H)

EXAMPLE 13

2-[4-(3,5-Difluorobenzyloxy)phenoxy]-5-ethoxyaniline hydrochloride $^1$H-NMR (DMSO-d$_6$, 200 MHz) δ (ppm); 1.29 (t, J=7 Hz, 3H), 3.95 (q, J=7 Hz, 2H), 5.11 (s, 2H), 6.42–6.58 (m, 1H), 6.65–6.83 (m, 2H), 6.95 (d, J=7 Hz, 2H), 7.00–7.05 (m, 3H), 7.15–7.28 (m, 3H)

EXAMPLE 14

2-[4-(2.5-Difluorobenzyloxy)phenoxy]-5-isopropoxyaniline hydrochloride $^1$H-NMR (DMSO-d$_6$, 200 MHz) δ (ppm); 1.24 (d, J=6 Hz, 6H), 4.48 (sext, J=6 Hz, 1H), 5.10 (s, 2H), 6.58 (dd, J=3, 9 Hz, 1H), 6.76 (d, J=9 Hz, 1H), 6.81 (d, J=3Hz, 1H), 6.96 (d, J=9 Hz, 2H), 7.07 (d, J=9 Hz, 2H), 7.20–7.47 (m, 3H)

EXAMPLE 15

2-[4-(3-Nitrobenzyloxy)phenoxy]aniline hydrochloride (1) To a solution of 4-(2-nitrophenoxy)phenol (1.00 g, 4.3 mmol) in ethanol (50 ml) were added an iron powder (1.21 g, 0.022 g-atom) and a solution of ammonium chloride (0.14 g, 2.6 mmol) in water (10 ml), followed by reflux for 2 hours. The insoluble matter was filtered, and the solvent was evaporated under reduced pressure. The residue was dissolved in ethyl acetate, and after drying, the solvent was evaporated under reduced pressure to give 4-(2-aminophenoxy)phenol (0.85 g).

(2) To a solution of 4-(2-aminophenoxy)phenol (0.85 g, 4.2 mmol) in N,N-dimethylformamide (20 ml) were added 3-nitrobenzyl chloride (0.87 g, 5.1 mmol), potassium iodide (0.70 g, 4.2 mmol) and potassium carbonate (0.88 g, 6.4 mmol), followed by stirring at 50° C. for 3 hours. The reaction solution was poured into water and extracted with ethyl acetate, and the organic layer was washed with water and a saturated aqueous sodium chloride solution. After drying, the solvent was evaporated under reduced pressure, and the residue was purified by silica gel column chromatography (eluent; chloroform) to give 2-[4-(3-nitrobenzyloxy)phenoxy]aniline (0.64 g)

(3) 2-[4-(3-Nitrobenzyloxy)phenoxy]aniline (0.64 g, 1.9 mmol) was dissolved in ethyl acetate (10 ml), and 4 N hydrogen chloride-ethyl acetate solution (1 ml) was added, followed by stirring for 30 minutes. The solvent was evaporated under reduced pressure, and the residue was crystallized from diethyl ether to give the title compound (0.55 g).

$^1$H-NMR (DMSO-d$_6$, 200 MHz) δ (ppm); 4.52 (s, 2H) 6.50–6.67 (m, 3H), 6.75–6.87 (m, 5H), 7.63 (t, J=8 Hz, 1H), 7.65 (br, 3H), 7.83 (d, J=8 Hz, 1H), 8.11 (d, J=8 Hz, 1H), 8.24 (s, 1H)

EXAMPLE 16

2-[4-(2-Fluorobenzyloxy)phenoxy]aniline hydrochloride (1) To a solution of 4-(2-nitrophenoxy)phenol (462 mg, 2.0 mmol) in N,N-dimethylformamide (20 ml) were added 2-fluorobenzyl bromide (400 mg, 2.1 mmol), potassium iodide (40 mg, 0.24 mmol) and potassium carbonate (300 mg, 2.2 mmol), followed by stirring at 50° C. for 4 hours. The reaction solution was poured into water and extracted with ethyl acetate. The organic layer was washed with water and a saturated aqueous sodium chloride solution and dried. The solvent was evaporated under reduced pressure to give 1-[4-(2-fluorobenzyloxy)phenoxy]-2-nitrobenzene (0.65 g).

$^1$H-NMR (CDCl$_3$, 200 MHz) δ (ppm); 5.13 (s, 2H), 6.93 (d, J=9 Hz, 1H), 7.01 (s, 4H), 7.05–7.55 (m, 6H), 7.93 (d, J=8 Hz, 1H)

(2) To a solution of 1-[4-(2-fluorobenzyloxy)phenoxy]-2-nitrobenzene (0.65 g, 1.9 mmol) in ethanol (50 ml) were added an iron powder (0.53 g, 9.5 mg-atom) and a solution of ammonium chloride (0.06 g, 1.1 mmol) in water (10 ml), followed by reflux for 3 hours. The insoluble matter was removed by filtration, the solvent was evaporated under reduced pressure, and the residue was dissolved in ethyl acetate. After drying, the solvent was again evaporated under reduced pressure, the residue was dissolved in a small amount of ethyl acetate, and 4 N hydrogen chloride-ethyl acetate solution (2 ml) was added, followed by stirring for 30 minutes. The solvent was evaporated under reduced pressure, and crystallization from diethyl ether gave the title compound (0.62 g).

m.p. 154–154.6° C.

EXAMPLE 17

2-[4-(2,5-Dichlorobenzyloxy)phenoxy]aniline hydrochloride

The title compound was obtained from 4-(2-nitrophenoxy)phenol and 2,5-dichlorobenzyl bromide in the same manner as in Example 16.

$^1$H-NMR (DMSO-d$_6$, 200 MHz) δ (ppm); 5.14 (s, 2H), 6.80 (d, J=9 Hz, 1H), 7.05–7.19 (m, 6H), 7.40 (dd, J=2, 8 Hz, 1H), 7.49 (dd, J=2, 8 Hz, 1H), 7.58 (d, J=8 Hz, 1H), 7.70 (d, J=2 Hz, 1H)

EXAMPLE 18

2-[4-(2,5-Difluorobenzyloxy)phenoxy]-5-ethoxyaniline

To a solution of 5-ethoxy-2-(4-hydroxyphenoxy)aniline (3.68 g, 15 mmol) in N,N-dimethylformamide (50 ml) were added potassium tert-butoxide (2.02 g, 18 mmol) and 2,5-difluorobenzyl bromide (3.11 g, 15 mmol), followed by stirring at room temperature overnight. The reaction solution was poured into water and extracted with ethyl acetate. The organic layer was washed with water and a saturated aqueous sodium chloride solution, and after drying, the solvent was evaporated under reduced pressure. The residue was purified by silica gel column chromatography [eluent; ethyl acetate-hexane (1:4)] to give the title compound (4.29 g).

m.p. 72–73.5° C.

EXAMPLE 19

2-[4-(2,5-Difluorobenzyloxy)phenoxy]aniline

The title compound was obtained from 2-(4-hydroxyphenoxy)aniline and 2,5-difluorobenzyl bromide in the same manner as in Example 18.

m.p. 59.5–60.5° C.

EXAMPLE 20

2-[4-(2,6-Difluorobenzyloxy)phenoxy]-5-ethoxyaniline

The title compound was obtained from 5-ethoxy-2-(4-hydroxyphenoxy)aniline and 2,6-difluorobenzyl bromide in the same manner as in Example 18.

m.p. 245–246° C.

EXAMPLE 21

2-[4-(2.6-Difluorobenzyloxy)phenoxy]aniline

The title compound was obtained from 2-(4-hydroxyphenoxy)aniline and 2,6-difluorobenzyl bromide in the same manner as in Example 18.

m.p. 88–89° C.

EXAMPLE 22

2-[4-(2,5-Difluorobenzyloxy)phenoxy]-5-methoxyaniline hydrochloride

2-[4-(2,5-Difluorobenzyloxy)phenoxy]-5-methoxyaniline prepared from 2-(4-hydroxyphenoxy)-5-methoxyaniline and 2,5-difluorobenzyl bromide in the same manner as in Example 18 was dissolved in ethyl acetate, and allowed to form the hydrochloric acid salt with 4 N hydrogen chloride-ethyl acetate solution to give the title compound.

m.p. 203–204° C.

EXAMPLE 23

2-[4-(2,6-Difluorobenzyloxy)phenoxy]-5-methoxyaniline hydrochloride

2-[4-(2,6-Difluorobenzyloxy)phenoxy]-5-methoxyaniline prepared from 2-(4-hydroxyphenoxy)-5-methoxyaniline and 2,6-difluorobenzyl bromide in the same manner as in Example 18 was dissolved in ethyl acetate, and allowed to form the hydrochloric acid salt with 4 N hydrogen chloride-ethyl acetate solution to give the title compound.

m.p. 193–194° C.

Experiment 1

Inhibitory Action on a $Na^+/Ca^{2+}$ Exchange System using Cardiac Sarcolemmal Vesicles Sarcolemmal vesicles prepared from the removed dog ventricular muscles according to the method described in the literature (L. R. Jones, Methods, Enzymol., 1988, 157, pp. 85) were used.

A $Na^+/Ca^{2+}$ exchange activity using the sarcolemmal vesicles was measured according to the method described in the literature (K. D. Philipson, et al., J. Biol. Chem., 1980, 255, pp. 6880). First, the sarcolemmal vesicles were suspended in a sodium-containing solution [160 mM sodium chloride, 20 mM Tris-hydrochloric acid (pH 7.4)] to make up to a protein concentration of 1.5 mg/ml, and allowed to stand for an hour to load $Na^+$ in the sarcolemmal vesicles. To 2.5 μl of the sarcolemmal vesicles was added 125 μl of a [$^{45}$Ca]-calcium chloride solution [20 μM [$^{45}$Ca]-calcium chloride, 160 mM potassium chloride and 20 mM Mops-Tris (pH 7.4)], and after 10 seconds, 900 μl of an ice-cooled lanthanum chloride solution [10 mM lanthanum chloride, 160 mM potassium chloride and 20 mM Mops-Tris (pH 7.4)] was added. The sarcolemmal vesicles were recovered on a nitrocellulose filter by suction filtration and washed three times with 900 μl of a lanthanum chloride solution. The 2+concentration of $Ca^{2+}$ uptake in the sarcolemmal vesicles was determined by measuring a $^{45}$Ca radioactivity by a scintillator. In addition, a $Na^+/Ca^{2+}$ exchange activity-independent $Ca^{2+}$ uptake in the sarcolemmal vesicles was determined by carrying out the same procedure using a potassium-containing solution [160 mM potassium chloride, 20 mM Tris-hydrochloric acid (pH 7.4)] instead of the sodium-containing solution.

The test compound was used as a dimethyl sulfoxide solution thereof, and its inhibitory effect was evaluated in comparison with the vehicle-treated group. The results are shown in Table 2.

TABLE 2

| Compound Number | $Na^+/Ca^{2+}$ exchange activity (% of control) |
|---|---|
| 3 | 38 |
| 4 | 27 |
| 5 | 43 |
| 6 | 39 |
| 7 | 33 |
| 8 | 47 |
| 10 | 45 |

*: The concentration of the test drug is 1 μM.

What is claimed is:

1. A 2-phenoxyaniline derivative represented by Formula (1):

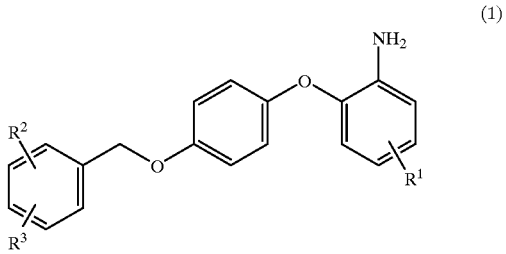

wherein $R^1$ is a hydrogen atom or a lower alkoxy group, $R^2$ is a halogen atom or a nitro group, and $R^3$ is a hydrogen atom or a halogen atom, or a pharmaceutically acceptable salt thereof.

2. The 2-phenoxyaniline derivative or the pharmaceutically acceptable salt thereof according to claim 1, wherein $R^1$ in Formula (1) is an ethoxy group or a propoxy group.

3. The 2-phenoxyaniline derivative or the pharmaceutically acceptable salt thereof according to claim 1, wherein $R^2$ and $R^3$ in Formula (1) are the same or different, and are each a halogen atom.

4. A pharmaceutical composition containing the 2-phenoxyaniline derivative or the pharmaceutically acceptable salt thereof according to claim 1 as an effective component.

5. The 2-phenoxyaniline derivative or the pharmaceutically acceptable salt thereof according to claim 1 for use as a pharmaceutically active component.

6. An inhibitor of a $Na^+/Ca^{2+}$ exchange system containing the 2-phenoxyaniline derivative or the pharmaceutically acceptable salt thereof according to claim 1 as an effective component.

7. A pharmaceutical composition for the treatment or prevention of ischemic heart diseases, ischemic cerebral diseases or ischemic renal diseases containing the 2-phenoxyaniline derivative or the pharmaceutically acceptable salt thereof according to claim 1 as an effective component.

8. A method of using the 2-phenoxyaniline derivative or the pharmaceutically acceptable salt thereof according to claim 1 for the manufacture of a pharmaceutical composition for the treatment or prevention of ischemic heart diseases, ischemic cerebral diseases or ischemic renal diseases.

9. A method for the treatment or prevention of ischemic heart diseases, ischemic cerebral diseases or ischemic renal diseases which comprises the step of administering a pharmacologically effective amount of the 2-phenoxyaniline derivative or the pharmaceutically acceptable salt thereof according to claim 1 to a human.

10. A pharmaceutical composition for the protection of cells during thrombolytic therapy, angioplasty, bypass operation of coronary artery or organ transplantation containing the 2-phenoxyaniline derivative or the pharmaceutically acceptable salt thereof according to claim 1 as an effective component.

11. A method of using the 2-phenoxyaniline derivative or the pharmaceutically acceptable salt thereof according to claim 1 for the manufacture of a pharmaceutical composition for the protection of cells during thrombolytic therapy, angioplasty, bypass operation of coronary artery or organ transplantation.

12. A method for the protection of cells during thrombolytic therapy, angioplasty, bypass operation of coronary artery or organ transplantation which comprises the step of administering a pharmacologically effective amount of the 2-phenoxyaniline derivative or the pharmaceutically acceptable salt thereof according to claim 1 to a human.

\* \* \* \* \*